United States Patent [19]

Proietto et al.

[11] Patent Number: 5,068,064
[45] Date of Patent: Nov. 26, 1991

[54] N-SUBSTITUTED LAURAMIDES, THEIR PREPARATION AND COMPOSITIONS IN WHICH THEY ARE PRESENT

[75] Inventors: Vincenzo Proietto, Saint Georges D'Orques; Ali Salhi, Saint Gely du Fesc, both of France

[73] Assignee: Sanofi, Paris, France

[21] Appl. No.: 534,497

[22] Filed: Jun. 7, 1990

[30] Foreign Application Priority Data

Jun. 8, 1989 [FR] France .............................. 89 07619

[51] Int. Cl.$^5$ .............................................. C09F 7/00
[52] U.S. Cl. .................................. 260/404.5; 260/404; 514/625; 424/406
[58] Field of Search ........................... 260/404, 404.5; 424/406; 514/625

[56] References Cited

U.S. PATENT DOCUMENTS

| | | | |
|---|---|---|---|
| 2,369,817 | 2/1945 | Groote et al. | 260/404.5 |
| 3,145,137 | 8/1964 | Newallis et al. | 260/404.5 |
| 3,145,137 | 8/1964 | Newallis et al. | 260/404.5 |

FOREIGN PATENT DOCUMENTS 887813 7/1949 Fed. Rep. of Germany .
1207803 2/1960 France .
2239 10/1962 France .

OTHER PUBLICATIONS

Chemical Abstracts, vol. 101, p. 351, 1984, 87319m.

*Primary Examiner*—Jose G. Dees
*Assistant Examiner*—Deborah D. Carr
*Attorney, Agent, or Firm*—Foley & Lardner

[57] ABSTRACT

The invention relates to N-substituted lauramides. These compounds have the formula

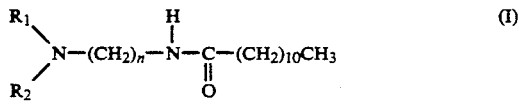

in which $R_1$ is a benzyl group and $R_2$ is an alkyl having from 1 to 4 carbon atoms, or $R_1$ and $R_2$ form a 4-benzyl-piperidino group with the nitrogen atom to which they are bonded, and $n=2$ to 6, or one of its salts with organic or mineral acids. Application: Preparation of compositions for antiseptic or antimicrobial use, or disinfectants and preservatives, especially in the sectors of pharmacy, cosmetology or agri-foodstuffs.

10 Claims, No Drawings

N-SUBSTITUTED LAURAMIDES, THEIR PREPARATION AND COMPOSITIONS IN WHICH THEY ARE PRESENT

The present invention relates to novel lauric acid amide derivatives substituted by an alkylamino group.

The present invention further relates to the use of the compounds according to the invention in compositions for antiseptic or antimicrobial use, as disinfectants or preservatives, especially in the sectors of pharmacy, cosmetology or agri-foodstuffs.

A publication of Czechoslovak origin by Devinsky et al., Chem. Zvesti., 1983, 37(2), 263-271 describes lauric acid alkylaminoalkylamides of the formula

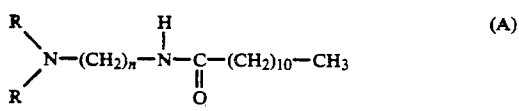

in which R=H, CH$_3$ or C$_2$H$_5$ and n=2 to 12.

Furthermore, three Czechoslovak patents by Devinsky et al. describe the compounds (B)

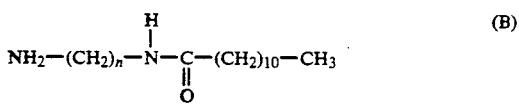

in which n=3-5 and 7-12, as corrosion inhibitors, dispersants and auxiliaries in the textile industry (Czechoslovak patent 220297, 1982-Chem. Abs. 105, 225810a), the compounds (C)

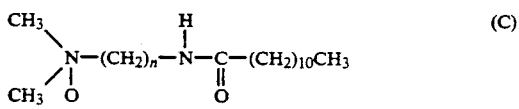

in which n=2 and 4-12, as auxiliaries in the textile industry and as possessing a bacteriostatic activity, without however specifying any values (Czechoslovak patent 220298, 1982-Chem. Abs. 105, 225811b), and the compounds (D)

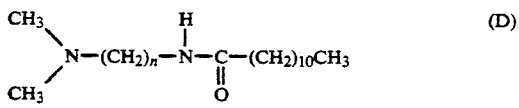

in which n=2, 4 and 12, as disinfectants, dispersants and local anesthetics (Czechoslovak patent 223443, 1982-Chem. Abs. 105, 208483d).

It has now been found that, in formula (A) in which R is hydrogen, replacement of one of these hydrogens with a benzyl group and the other with an alkyl, or replacement of both hydrogens together with a 3-benzyl-1,5-pentylene group so as to form a 4-benzylpiperidino group with the nitrogen, gives novel N-benzylaminoalkyllauramides having an excellent bactericidal activity superior to that of the corresponding dialkylaminoalkyl derivatives, and a good fungicidal activity.

The present invention therefore relates to aminoalkyllauramides of the formula

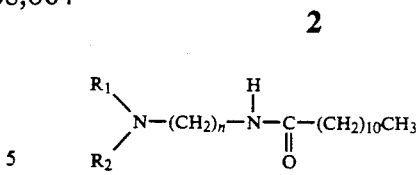

in which R$_1$ is a benzyl group and R$_2$ is an alkyl having from 1 to 4 carbon atoms, or R$_1$ and R$_2$ form a 4-benzylpiperidino group with the nitrogen atom to which they are bonded, and n is 2, 3, 4, 5 or 6, and to the salts of the compounds (I) with organic or mineral acids.

The compounds (I) in which n=2 or n=3 are preferred compounds.

The salts of the compounds of formula (I) according to the present invention include those with mineral or organic acids which permit suitable separation or crystallization of the compounds of formula (I), such as picric acid or oxalic acid, as well as those with mineral or organic acids which form salts acceptable in pharmaceutical, edible, cosmetic or disinfectant compositions, such as the hydrochloride, hydrobromide, sulfate, hydrogensulfate, dihydrogenphosphate, methanesulfonate, methylsulfate, maleate, fumarate and naphthalene-2-sulfonate.

According to another of its features, the present invention relates to a process for the preparation of the compounds of formula (I), which comprises reacting an amine

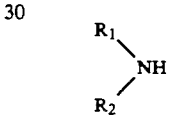

with a nitrile of the formula $$X-CN \quad (1)$$

in which X is a group selected from chloromethyl, 2-chloroethyl, 2-chlorovinyl, 3-chloropropyl, 4-chlorobutyl and 5-chloropentyl groups, to give the nitrile intermediate of the formula

in which m is n−1, n being as defined above, subjecting the resulting product to catalytic hydrogenation, treating the resulting amino derivative of the formula

with lauroyl chloride and, if desired, converting the resulting product to one of its salts.

The compounds (I) according to the invention are prepared by reacting the amine

with a nitrile $$X-CN \qquad (1)$$

either, if X is a vinyl group, in an alkanol such as, for example, ethanol, the reaction mixture being stirred for 2 to 4 hours at room temperature, or, if X is other than a vinyl group, in an inert solvent such as, for example, toluene or benzene, in which the nitrile is dissolved, in the presence of a base such as triethylamine, the amino derivative then being added slowly to this solution at room temperature, to give the nitrile intermediate of formula (2)

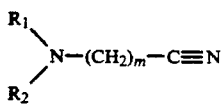

in which $R_1$, $R_2$ and m are as defined above. Acrylonitrile and chloroacetonitrile are advantageously used as compounds of formula (1).

This nitrile intermediate is then reduced at room temperature and atmospheric pressure by catalytic hydrogenation in the presence of a catalyst such as, for example, Raney nickel or lithium aluminum hydride, in an alkanol such as, for example, ethanol, in the presence of ammonia.

The resulting amino intermediate of formula (3)

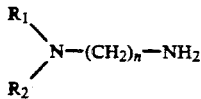

is then dissolved in an inert solvent such as, for example, methylene chloride, in the presence of a base such as, for example, triethylamine. Lauroyl chloride dissolved in methylene chloride, for example, is then added to this solution and the reaction takes place virtually instantaneously at room temperature.

The resulting product of formula (I) is isolated, in the form of the free base or a salt, by the conventional techniques.

If the compound of formula (I) is obtained in the form of the free base, salt formation is effected by treatment with the chosen acid in an organic solvent. Treatment of the free base, dissolved in an alcohol such as isopropanol, for example, with a solution of the chosen acid in the same solvent gives the corresponding salt, which is isolated by the conventional techniques. The hydrochloride, hydrobromide, sulfate, hydrogensulfate, dihydrogenphosphate, methanesulfonate, methylsulfate, oxalate, maleate, fumarate and naphthalene-2-sulfonate, for example, are prepared in this way.

When the reaction is complete, the compound of formula (I) can be isolated in the form of one of its salts, for example the hydrochloride or the oxalate; in this case, if necessary, the free base can be prepared by neutralization of said salt with a mineral or organic base such as sodium hydroxide or triethylamine, or with an alkali metal carbonate or bicarbonate such as sodium or potassium carbonate or bicarbonate.

The following examples illustrate the invention without however limiting it.

The melting points (m.p.) are expressed in degrees Celsius and were determined with a Tottoli apparatus; the yields Y are expressed in %; m denotes the weights obtained.

EXAMPLE 1

N-(3-Benzylmethylaminopropyl)lauramide hydrochloride: SR 45583 A

A) 3-(Benzylmethylamino)propionitrile 5.3 g of acrylonitrile are added dropwise to a solution of 12.1 g of N-benzylmethylamine in 20 ml of ethanol. The reaction mixture is stirred for three hours at room temperature and then concentrated under vacuum to give 17 g (Y=97%) of the expected product.

B) 3-(Benzylmethylamino)propylamine 17 g of the product obtained according to A) are dissolved in a mixture of 200 ml of ethanol, 20 ml of water and 40 ml of ammonia and hydrogenated at room temperature and atmospheric pressure in the presence of Raney nickel.

When the theoretical volume of hydrogen has been absorbed, the catalyst is filtered off and the filtrate is concentrated under vacuum. The residue is solubilized in hot ethanol and the precipitate is then filtered off and washed with ether.

m=20 g—Y=80%

C) SR 45583 A 4.2 g of lauroyl chloride are added dropwise to a solution of 5 g of the product obtained according to B) and 6 g of triethylamine in 100 ml of methylene chloride. The reaction mixture is stirred overnight at room temperature and then concentrated. The residue is taken up in water and then extracted with ethyl ether and the extract is washed with water, dried over magnesium sulfate and concentrated under vacuum.

7 g (Y=94%) of base are obtained which are dissolved in acetone, a solution of hydrogen chloride in ether is then added and the hydrochloride is filtered off and recrystallized from a mixture of isopropanol and ether. The hydrochloride is filtered off, washed with acetone and dried under vacuum.

m=4.7 g

M.p.=113°–115° C.

EXAMPLE 2

N-[2-(4-Benzylpiperidino)ethyl]lauramide hydrochloride: SR 44944 A

A) (4-Benzylpiperidino)acetonitrile 40.8 ml of triethylamine and 22.2 g of chloroacetonitrile are dissolved in 180 ml of toluene, and 51.6 g of 4-benzylpiperidine are then added dropwise all at once.

The temperature of the mixture rises and triethylamine hydrochloride precipitates. After a reaction time of 2 hours, the mixture is concentrated under vacuum, the residue is taken up in 600 ml of ethyl ether and the triethylamine hydrochloride is filtered off.

The filtrate is washed with a saturated solution of sodium bicarbonate, then with water and then with a saturated solution of sodium chloride, dried over magnesium sulfate, filtered and concentrated under vacuum.

The residue is distilled under reduced pressure.

m=40 g

Boiling point under 0.03 mbar=136° C.

B) 1-(2-Aminoethyl)-4-benzylpiperidine dihydrochloride 22 g of the product obtained above, dissolved in a mixture of 250 ml of ethanol, 30 ml of water and 100 ml of ammonia, are hydrogenated at room temperature and atmospheric pressure in the presence of a catalytic amount of Raney nickel.

After 4 hours, the catalyst is filtered off and the filtrate is evaporated under reduced pressure. The residue is dissolved in 500 ml of methylene chloride, and 50 ml of a solution of hydrogen chloride in ether are added. The hydrochloride is filtered off and rinsed with acetone.

m=22 g
M.p.=176°-180° C.

C) SR 44944 A 20.38 g of the product obtained above and 29.1 ml of triethylamine are dissolved in 400 ml of methylene chloride.

A solution of 16.65 ml of lauroyl chloride in 50 ml of methylene chloride is then added.

The reaction is virtually instantaneous.

The solvent is concentrated under vacuum, the residue is taken up in ethyl ether and the triethylamine hydrochloride is filtered off.

The filtrate is washed with water, then with a saturated solution of sodium bicarbonate and then with water until the pH of the washings is neutral.

The ether phase is dried over magnesium sulfate and then concentrated under vacuum. The residue is taken up in 250 ml of acetone, and 20 ml of a solution of hydrogen chloride in ether are added. The hydrochloride is filtered off.

m=25.6 g—Y=76%
M.p.=103° C.

The compounds collated in Table I were synthesized according to Examples 1 or 2.

$$CH_3\diagdown\atop CH_3\diagup N-CH_2CH_2-\underset{\overset{|}{}}{N}-\underset{\overset{\|}{O}}{C}-(CH_2)_{10}CH_3 \quad (D_1)$$

was synthesized and studied.

In the two methods, a bacterial inoculum is brought into contact with different dilutions of the product for a determined period of time.

When the contact period has ended, an aliquot of the mixture of bacterial suspension and product is taken and brought into contact with an agent for neutralizing the bacterial activity of the mixture, either in a solid medium or in a liquid medium. The bactericidal activity of the product, expressed either as a concentration or as a percentage of active principle, corresponds to an absence of bacterial growth.

The first method makes it possible to define a minimum bactericidal concentration (MBC) or minimum fungicidal concentration (MFC), expressed in μg/ml. The contact time between product and bacterial suspension is 30 minutes. The neutralizer is included in agar.

The CIP bacterial strains chosen for the study, which are available from the Institut Pasteur, are:

| | |
|---|---|
| 1. Staphylococcus aureus | CIP 53154 |
| 2. Enterococcus faecium | CIP 5855 |
| 3. Escherichia coli | CIP 54127 |
| 4. Psuedomonas aeruginosa | CIP A22 |

TABLE I $$\underset{R_2}{\overset{R_1}{\diagdown}}N-(CH_2)_n-NH-\underset{\overset{\|}{O}}{C}-(CH_2)_{10}-CH_3$$

| SR n°<br>Example n° | $\underset{R_2}{\overset{R_1}{\diagdown}}N-$ | n | M.p., °C.<br>base or salt | Recrystallization solvent |
|---|---|---|---|---|
| 45320 A<br>3 | benzyl-piperidinyl (C₆H₅–CH₂–⟨piperidine⟩N–) | 3 | 150–152<br>hydrochloride | acetone/ethyl ether |
| 45525<br>4 | CH₃(benzyl)N– (CH₃ and H₂C–C₆H₅ on N) | 2 | 104–106<br>base | acetone/ethyl ether |

The bactericidal and fungicidal activity of the products according to the invention was studied on different microbial strains by two methods.

For the purpose of comparing it with the compounds forming the subject of the invention, the product described in Czechoslovak patent 223,443:

The strains are maintained on Tryptic Soy Agar ® (TSA) marketed by Difco.

After 24 hours of culture at 37° C., the microbial growth is harvested with the aid of glass beads and 10 ml of diluent containing 1 g of tryptone and 8.5 g of sodium chloride in 1000 ml of distilled water. The suspension formed is shaken and the percentage transmission of light at 620 nm is measured in a spectrophotometer:

Strain 1: 70%
Strain 2: 60%

Strain 3: 70%
Strain 4: 60%

The bacterial inoculum corresponds to a 1:20 dilution of this bacterial suspension.

Plates containing cupules receive different dilutions of the test product. These dilutions of the test product are brought into contact with the different bacterial suspensions using a multiple site inoculator. After a contact time of 30 minutes, aliquots are transferred with this inoculator to the surface of an agar medium (TSA) placed in Petri dishes containing an activity neutralizer, namely 20 g of lubrol W, 2.5 g of Tween 80, 2.5 g of sodium thiosulfate and 1% of egg yolk in 1000 ml of TSA (Difco). A control for the efficacy of the neutralizer is prepared for each test product by depositing an aliquot of the dilution of the test product on the surface of the culture medium. After drying, the corresponding inoculum is deposited in the same place. An inoculum control is prepared on agar medium with and without neutralizer. The results are read off after 48 hours of incubation at 37° C.

The antifungal activity of the products according to the invention was also determined using the method described above. A representative strain of yeast was selected for the study: *Candida albicans* CIP 1180 (strain 5).

This is maintained on Sabouraud's Dextrose Agar marketed by Difco. The technique is identical to that described for studying the antibacterial activity. After 48 hours of culture at 37° C., the microbial growth is harvested with the aid of glass beads and 5 ml of diluent containing 1 g of tryptone and 8.5 g of sodium chloride in 1000 ml of distilled water; a further 5 ml of the diluent are then added. This suspension gives a percentage transmission of light at 620 nm of 2 to 3% in a spectrophotometer.

The inoculum corresponds to a 1:10 dilution of this microbial suspension. A 1:100 dilution of this suspension, observed between slide and cover glass through a No. 40 microscope objective, must show 10 cells per field, which corresponds to 1,000,000 yeasts per ml.

The results are collated in Table II. They indicate the minimum bactericidal concentrations (MBC) for strains 1, 2, 3 and 4 and the minimum fungicidal concentrations (MFC) for strain 5.

TABLE II

Minimum bactericidal and fungicidal concentrations in $\mu g/ml$

| Product solubility | S. aureus CIP 53154 | E. faecium CIP 5855 | E. coli CIP 54127 | P. aeruginosa CIP A22 | C. albicans CIP 1180 |
|---|---|---|---|---|---|
| D$_1$ 1.8% in H$_2$O | 50 | 50 | 50 | 50 | 200 |
| SR 45320 A 1% in TEG | 10 | 10 | 10 | 10 | 10 |
| SR 45525 >5% in H$_2$O | 50 | 10 | 10 | 50 | 50 |
| SR 45583 A >5% in H$_2$O | 50 | 10 | 10 | 50 | 50 |
| SR 44944 A 1% in acetone | 10 | 10 | 10 | 50 | 10 |

TEG = tetraethylene glycol

The products are all more active than the product of the prior art, D$_1$, irrespective of the strain studied, the greatest difference being observed in respect of *Candida albicans*. The product having the lowest MBC and MFC is SR 45320 A.

The second method makes it possible to define a percentage of bactericidal or fungicidal active principle by means of a simplified and automated adaptation of Afnor standards NF T 72-150 and NF T 72-170. In this method, the bactericidal activity of the product is determined with and without interfering substances. It is based on assessing the destruction of 99.99% of the initial bacteria by the product in 5 minutes. The interfering substances are of the protein type and are chosen for the actual conditions of application of this type of product. The contact time between product and bacterial suspension is 5 minutes, the neutralization step is 10 minutes and subculture is effected in a liquid medium.

The chosen bacterial strains are:

| 1. *Staphylococcus aureus* | CIP 53154 |
|---|---|
| 2. *Enterococcus faecium* | CIP 5855 |
| 3. *Escherichia coli* | CIP 54127 |
| 4. *Pseudomonas aeruginosa* | CIP A22 |
| 5. *Mycobacterium smegmatis* | CIP 7326 |

The strains are maintained on Tryptic Soy Agar ® (TSA) marketed by Difco.

The strains are harvested in a manner identical to the first method; these suspensions contain between $1.10^8$ and $3.10^8$ cells per milliliter. Appropriate dilutions make it possible to have a suspension containing 2 to $6.10^3$ cells per milliliter.

The experiment is performed in microtiter plates; it comprises two steps. The first step, called the preliminary test, checks that the product is indeed neutralized. In the test proper, the different dilutions of the product are brought into contact with 2 to $6.10^3$ cells per milliliter of the bacterial suspension in the second row of the microtiter plate. After a contact time of 5 minutes, an aliquot is transferred to the third row containing the neutralizer adapted to the product and to the strain. After a contact time of 10 minutes, aliquots are transferred to the last 5 rows containing Tryptic Soy Broth ® (TSB) from Difco.

The interfering substances tested are a mixture of albumin and yeast extract. In the first row of the microplate, these proteins are brought into contact for 5 minutes with the different dilutions of the product. After this step, the same principle as above is applied: 5 minutes of contact with the germ, 10 minutes of contact with the neutralizer, transfer to TSB.

The antifungal activity of the products according to the invention was also determined with and without interfering substances using the method described above. The same strain was used as for the first technique, namely *Candida albicans* CIP 1180. It is harvested in an identical manner to that described in the first method.

The results are collated in Table III.

TABLE III

| Strain | Method | D$_1$ | SR 45320A | SR 45525A | SR 45583A | SR 44944A |
|---|---|---|---|---|---|---|
| S. aureus | Simple (1) | 0.1–0.05* | 0.005 | 0.05 | 0.05 | <0.01 |
| 53154 CIP | Proteins (2) | 0.5 | 0.05 | 0.5 | 0.5 | 0.1 |
| E. faecium | Simple (1) | 0.01 | <0.001 | 0.01 | 0.01 | <0.01 |
| 5855 CIP | Proteins (2) | 0.1 | 0.1 | 0.5 | 0.05 | 0.03 |
| E. coli | Simple (1) | 0.05 | 0.01 | 0.005 | 0.05 | 0.01 |
| 54127 CIP | Proteins (2) | 0.1 | 0.05 | 0.1 | 0.1 | <0.01 |
| P. aeruginosa | Simple (1) | 0.05 | 0.005 | 0.005 | 0.01 | <0.01 |
| A22 CIP | Proteins (2) | 0.5 | >0.5 | 0.5 | 0.5 | 0.25 |
| C. albicans | Simple (1) | 0.1 | 0.005 | 0.05 | 0.05 | 0.01 |
| 1180 CIP | Proteins (2) | 0.5 | 0.05 | 0.05 | 0.1 | 0.06 |
| M. smegmatis | Simple (1) | 0.1–0.05* | 0.1–0.005 | 0.1–0.01* | 0.01 | >0.5 |
| 7326 CIP | Proteins (2) | >0.5 | 0.05 | 0.1 | 0.05 | 0.06 |

*activity limited to the zone indicated
(1) without interfering substances
(2) with proteins as interfering substances The product D$_1$ of the prior art is that for which the activities are the lowest.

These results show that the products according to the invention possess an advantageous and rapid antifungal activity.

The tolerance of the products according to the invention was studied on guinea-pigs. The animals are shaved on either side of the median line of the back and shaving is repeated every 2 days. Groups of 6 animals receive 0.2 ml of an aqueous or alcoholic solution of the product according to the invention on the shaved area. If the products are in alcoholic solution, a control group of animals receives the alcohol on one side.

To study the skin tolerance, the treatment is applied once a day for 6 out of 7 days over 3 weeks. The observations pertaining to the skin concern the presence of erythema, skin eruption or hyperkeratosis, the intensity of which is graded according to a fixed scale.

The skin sensitization test is performed on the same animals after two weeks' rest. The treatment lasts one week and is identical to the previous treatment. Evaluation is made according to the same criteria and on the same scale as that used for the local tolerance.

It was found that the products according to the invention are well tolerated when they are applied at concentrations ranging up to 2% by weight. Furthermore, they have no sensitizing effect.

The acute toxicity was evaluated by oral administration to mice. This study was performed on male mice of the CD1 strain originating from the Charles River breed. Each group was made up of 5 animals with a body weight varying between 24 and 30 g, kept in the same cage. The animals were fasted for 6 hours before the treatment. For each study, a suspension of the product in a 10% solution of gum arabic was administered by force-feeding using a stomach tube. The animals were given food again 4 hours after force-feeding and were kept under observation for a period of 14 days after administration. During this period, the mortality in each of the experimental groups was noted and, where possible, the 50% lethal dose (LD$_{50}$) was determined using the method of J. T. LITCHFIELD and R. WILCOXON, J. Pharmacol. 1949, 95, 99–113. The LD$_{50}$ per os of the products according to the invention was found to be greater than 1000 mg/kg.

The products according to the invention, which have a good antimicrobial activity, can be used in pharmaceutical, disinfectant, cosmetic or edible preparations, especially as antiseptics by local and general administration, as disinfectants and as preservatives.

As antiseptics for human or veterinary use, the concentration of active product can vary from 0.01% to 5% by weight, according to the use and the chosen formulation. Thus it is possible to prepare detergent foaming solutions with which the surgeon and nursing staff can wash their hands or which are intended for the cleansing of dermatological lesions such as impetigo, pityriasis and leg ulcers. Detergent foaming solutions are also used as shampoos (for example antidandruff shampoos) or for the preparation of shower gels, shaving creams and foaming lotions. Foaming solutions containing products according to the invention are obtained by using amphoteric, anionic, cationic or nonionic surfactants at a concentration of 0.3 to 30%, humectants, such as glycols or polyethylene glycols, at a concentration of 0 to 20%, copolymers of ethylene oxide and polypropylene at a concentration of 0 to 20%, and an alcohol (ethanol, isopropanol, benzyl alcohol) or a polyol, such as glycerol, at a concentration of 0 to 15%, as well as agents for complexing Ca$^{++}$, Mg$^{++}$ and heavy metal ions, salts providing an appropriate buffer capacity, agents for imparting viscosity, such as NaCl or KCl, natural, cellulosic or synthetic polymers, such as polyvinylpyrrolidone, superfatting and thickening agents, such as polyethylene glycol distearate and copra monoethanolamide or diethanolamide, perfumes, preservatives and colorants.

If the product according to the invention is not readily soluble in water, it will be possible to use microemulsions, micellar solutions or any other phase of the ternary or quaternary diagram water/active principle/surfactant/cosurfactant (see Les Microémulsions (Microemulsions), LA RECHERCHE No. 167, June 1985) which permits solubilization in water. These solutions may or may not be diluted; they can be dispensed for example with the aid of a vasopump or liquefied or non-liquefied propellant gases.

With the same constituents at appropriate concentrations, products according to the invention can also be used to prepare simple aqueous solutions or aqueous solutions in the form of sprays intended for antisepsis of the operative fields, for postoperative treatment and for the treatment of burns, superinfected eczema, bed-sores, wounds or acne, or intended for deodorants.

Simple alcoholic solutions or alcoholic solutions in the form of sprays containing 20 to 80% of alcohol can contain, in addition to the excipients used in the aqueous solutions, excipients which make it possible to penetrate the keratinized layers of the skin and superficial body growths, such as Azone (marketed by Nelson Research)

and Transcutol (marketed by Gattefossé). These solutions are intended for antisepsis of the skin before puncturing, preparation of the operative field and antisepsis of the nursing staff's hands, or for the treatment of closed infected dermatosis, folliculitis, perionyxis or acne.

The products according to the invention can be applied in the form of creams which contain some of the compounds mentioned for the preparation of the solutions, as well as the fatty substances normally encountered in the preparation of creams or emulsions. These creams can be used especially for preventing superinfections of bed-sores, eczema, mycosis or acne.

The products according to the invention can also be used for the treatment or prevention of sexually transmitted diseases, in the form of pessaries, gynecological tablets or gynecological sponges or to complement contraceptives. The pessaries can contain from 0 to 99% of triglycerides, polyethylene glycols of different molecular weights, Tweens, natural or synthetic polymers, polyols and soaps. The gynecological tablets can contain diluents such as lactose or cellulose, lubricants such as magnesium stearate, flow enhancers such as silica, and disintegrating agents such as carboxymethyl starch or cellulose.

The products according to the invention can be administered in the form of sprays, with nasal and buccal nozzles, for the treatment of infectious syndromes of the respiratory tract (rhinitis, sinusitis, sore throat, amygdalitis, pharyngitis) or in the form of gels or mouthwashes for the treatment of gingivitis or pyorrhea or for the prevention of dental plaque, for which it will also be possible to use toothpastes containing the product according to the invention. The forms intended for buccal or nasal administration can contain the same excipients as the aqueous solutions described above, to which there may be added flavorings in the case of buccal administration or the constituents necessary for isotonicity in the case of the nasal sprays; the toothpastes also contain pyrogenic or non-pyrogenic colloidal silicas, calcium carbonate, sweeteners and fluorine salts.

The products according to the invention can be used in eye lotions, eye solutions or ophthalmic ointments for the treatment of eye infections (for example blepharitis or conjunctivitis) or in a liquid for rinsing contact lenses. These forms for the eyes can be prepared using the same constituents as those used for the solutions, care being taken to ensure that the mixture is isotonic.

Furthermore, the products according to the invention can be administered to man by a general route, for example orally, in the form of gelatin capsules, intestinal tablets or other tablets, as intestinal antiseptics.

The products according to the invention can also be used in animals for indications such as the prevention or treatment of infected lesions or lesions capable of becoming superinfected. The pharmaceutical compositions here are similar to those used in man and are, in particular, creams, sprays or solutions.

In another connection, the rapid lethal action of the products according to the invention against germs enables them to be used as surface disinfectants at concentrations which can vary from 0.1 to 4%. In this case, the products are used in preparations such as aqueous or non-aqueous, detergent foaming solutions, nasal sprays or other sprays. Such preparations are particularly useful in the hospital or veterinary sectors, for local organizations or for the agri-foodstuffs industries. These preparations can contain the same constituents as those employed in the formulations for antiseptic use, although a variety of organic solvents may be added.

Finally, the antimicrobial activity of these products enables them to be used as preservatives in the pharmaceutical, cosmetic and food industries. In this case, the products according to the invention are used as additives for pharmaceutical, cosmetic or edible formulations at concentrations which can vary from 0.005 to 0.5%. These compounds can also be used as disinfectant additives in paints.

EXAMPLE 5

Antiseptic, detergent, foaming liquid preparation

| | |
|---|---|
| SR 45320 A | 0.5 g |
| Sodium paraffinsulfonate | 15 g |
| Sodium hydroxide or lactic acid q.s. pH 5.2 | |
| Purified water q.s. | 100 g |

EXAMPLE 6

Antiseptic alcoholic solution

| | |
|---|---|
| SR 44944 A | 0.2 g |
| Alkyldimethylcarboxymethylamine (30% solution) | 0.5 g |
| Condensation product of ethylene oxide and propylene glycol L 62 | 1 g |
| Lactic acid or sodium hydroxide q.s. pH 6.5 | |
| 70° ethyl alcohol q.s. | 100 g |

EXAMPLE 7

Antiseptic, detergent, foaming liquid preparation

| | |
|---|---|
| SR 44944 A | 0.1 g |
| Alkyldimethylcarboxymethylamine (30% solution) | 15 g |
| Disodium tetracemate | 0.1 g |
| Propylene glycol | 20 g |
| Sodium hydroxide q.s. pH 5.8 | |
| Purified water q.s. | 100 g |

EXAMPLE 8

Oral medication

| | |
|---|---|
| SR 45320 A | 0.3 g |
| 95° ethyl alcohol | 14 g |
| Oil of aniseed | 0.00225 ml |
| Eugenol | 0.00075 ml |
| Glycerol | 20 ml |
| Saccharin | 0.03 g |
| Sodium hydroxide solution q.s. pH 5.5 | |
| Purified water q.s. | 100 ml |

EXAMPLE 9

Antiseptic pessaries intended for the treatment of sexually transmitted diseases

| | |
|---|---|
| SR 44944 A | 500 mg |
| Eutectic mixture of fatty acid esters | 2.568 g |

Suppocire A ®, marketed by Gattefossé, can be used as the eutectic mixture of fatty acid esters.

EXAMPLE 10

Eye lotion

| | |
|---|---|
| SR 45320 A | 0.2 g |
| Sodium chloride | 1.4 g |
| Water for injectable preparations q.s. | 100 ml |

EXAMPLE 11

Intestinal tablets

| | |
|---|---|
| SR 44944 A | 200 mg |
| Hydroxypropylmethyl cellulose 6 cP | 6 mg |
| Lactose | 114 mg |
| Microcrystalline cellulose | 60 mg |
| Sodium carboxymethyl starch | 12 mg |
| Magnesium stearate | 8 mg |
| For a finished uncoated tablet of | 400 mg |
| Coating | |
| Eudragit L 100 | 0.9 mg |
| Dibutyl phthalate | 0.9 mg |
| Acetone | 14.1 mg |
| Isopropyl alcohol | 14.1 mg |
| Finished coated tablet of | 430 mg |

EXAMPLE 12

Sprays

| | |
|---|---|
| SR 44320 A | 2 g |
| 95° ethanol | 20 g |
| Propylene glycol | 5 g |
| Sodium hydroxide q.s. | pH 5.5 |
| Water q.s. | 100 g |
| Propellent q.s. | |

EXAMPLE 13

Film-forming spray

| | |
|---|---|
| SR 44320 A | 0.5 g |
| Polyvinylpyrrolidone | 2 g |
| Acrylic resin | 2 g |
| 95° ethanol q.s. | 100 g |
| Propellant q.s. | |

EXAMPLE 14

A product according to the invention can be used as a preservative in a cream emulsion.

| | |
|---|---|
| Liquid paraffin | 6 g |
| Mixture of cetostearyl alcohol and ethoxylated cetostearyl alcohol | 9 g |
| Anhydrous monosodium phosphate | 0.300 g |
| Disodium tetracemate | 0.010 g |
| Petroleum jelly | 15 g |
| SR 44320 A | 0.100 g |
| Phosphoric acid q.s. | pH 4.5 |
| Purified water q.s. | 100 g |

EXAMPLE 15

The product according to the invention can be used as a preservative in a cream for cosmetological use.

| | |
|---|---|
| Collagen | 0.500 g |
| Carboxypolymethylene 934 | 0.400 g |
| Hydrogenated lanolin | 4 g |
| Perhydrosqualene | 20 g |
| Polyethoxylated sorbitol monopalmitate | 2 g |
| SR 44944 A | 0.150 g |
| Lactic acid or sodium hydroxide q.s. | pH 6.5 |
| Purified water q.s. | 100 g |

EXAMPLE 16

Preservative in an antisunburn oil

| | |
|---|---|
| Mineral oil 65/75 | 68 g |
| Castor oil | 8 g |
| Sesame oil | 20 g |
| Isopropyl alcohol | 2 g |
| Eusolex ® | 1.5 g |
| Perfume | 0.4 g |
| SR 44320 A | 0.100 g |

(Eusolex ® is marketed by Merck)

EXAMPLE 17

Preservative in a shampoo

| | |
|---|---|
| Potassium amino acid palmitate | 20 g |
| Sodium alkylsulfates | 2 g |
| Copra diethanolamide | 5 g |
| Linalyl acetate | 0.200 g |
| SR 44320 A | 0.05 g |
| Sodium hydroxide q.s. | pH 7 |
| Purified water q.s. | 100 g |

EXAMPLE 18

Preservative for fruit juice or jam

| | |
|---|---|
| Micronized SR 44944 A | 0.02% |

EXAMPLE 19

Disinfectant for inert surfaces

| | |
|---|---|
| SR 44320 A | 2 g |
| Dodecyldimethylcarboxydimethylamine | 20 g |
| Disodium tetracemate | 2 g |
| Lactic acid q.s. | pH 3.5 |
| Purified water q.s. | 100 g |

EXAMPLE 20

Antiseptic, detergent, foaming liquid preparation

| | |
|---|---|
| SR 45583 A | 0.5 g |
| Sodium paraffinsulfonate | 15 g |
| Sodium hydroxide or lactic acid q.s. | pH 5.2 |
| Purified water q.s. | 100 g |

EXAMPLE 21

Antiseptic alcoholic solution

| | |
|---|---|
| SR 45583 A | 0.2 g |
| Alkyldimethylcarboxymethylamine (30% solution) | 0.5 g |
| Condensation product of ethylene oxide and propylene glycol L 62 | 1 g |

-continued

| Lactic acid or sodium hydroxide q.s. | pH 6.5 |
|---|---|
| 70° ethyl alcohol q.s. | 100 g |

EXAMPLE 22

Antiseptic, detergent, foaming liquid preparation

| SR 45583 A | 0.1 g |
|---|---|
| Alkyldimethylcarboxymethylamine (30% solution) | 15 g |
| Disodium tetracemate | 0.1 g |
| Propylene glycol | 20 g |
| Sodium hydroxide q.s. | pH 5.8 |
| Purified water q.s. | 100 g |

EXAMPLE 23

Oral medication

| SR 45583 A | 0.3 g |
|---|---|
| 95° ethyl alcohol | 14 g |
| Oil of aniseed | 0.00225 ml |
| Eugenol | 0.00075 ml |
| Glycerol | 20 ml |
| Saccharin | 0.03 g |
| Sodium hydroxide solution q.s. pH 5.5 | |
| Purified water q.s. | 100 ml |

EXAMPLE 24

Antiseptic pessaries intended for the treatment of sexually transmitted diseases

| SR 45583 A | 500 mg |
|---|---|
| Eutectic mixture of fatty acid esters | 2.568 g |

Suppocire A ®, marketed by Gattefossé, can be used as the eutectic mixture of fatty acid esters.

EXAMPLE 25

Eye lotion

| SR 45583 A | 0.2 g |
|---|---|
| Sodium chloride | 1.4 g |
| Water for injectable preparations q.s. | 100 ml |

EXAMPLE 26

Intestinal tablets

| SR 45583 A | 200 mg |
|---|---|
| Hydroxypropylmethyl cellulose 6 cP | 6 mg |
| Lactose | 114 mg |
| Microcrystalline cellulose | 60 mg |
| Sodium carboxymethyl starch | 12 mg |
| Magnesium stearate | 8 mg |
| For a finished uncoated tablet of | 400 mg |
| Coating | |
| Eudragit L 100 | 0.9 mg |
| Dibutyl phthalate | 0.9 mg |
| Acetone | 14.1 mg |
| Isopropyl alcohol | 14.1 mg |
| Finished coated tablet of | 430 mg |

EXAMPLE 27

Sprays

| SR 45583 A | 2 g |
|---|---|
| 95° ethanol | 20 g |
| Propylene glycol | 5 g |
| Sodium hydroxide q.s. pH 5.5 | |
| Water q.s. | 100 g |
| Propellant q.s. | |

EXAMPLE 28

Film-forming spray

| SR 45583 A | 0.5 g |
|---|---|
| Polyvinylpyrrolidone | 2 g |
| Acrylic resin | 2 g |
| 95° ethanol q.s. | 100 g |
| Propellant q.s. | |

EXAMPLE 29

A product according to the invention can be used as a preservative in a cream emulsion.

| Liquid paraffin | 6 g |
|---|---|
| Mixture of cetostearyl alcohol and ethoxylated cetostearyl alcohol | 9 g |
| Anhydrous monosodium phosphate | 0.300 g |
| Disodium tetracemate | 0.010 g |
| Petroleum jelly | 15 g |
| SR 45583 A | 0.100 g |
| Phosphoric acid q.s. pH 4.5 | |
| Purified water q.s. | 100 g |

EXAMPLE 30

The product according to the invention can be used as a preservative in a cream for cosmetological use.

| Collagen | 0.500 g |
|---|---|
| Carboxypolymethylene 934 | 0.400 g |
| Hydrogenated lanolin | 4 g |
| Perhydrosqualene | 20 g |
| Polyethoxylated sorbitol monopalmitate | 2 g |
| SR 45583 A | 0.150 g |
| Lactic acid or sodium hydroxide q.s. pH 6.5 | |
| Purified water q.s. | 100 g |

EXAMPLE 31

Preservative in an antisunburn oil

| Mineral oil 65/75 | 68 g |
|---|---|
| Castor oil | 8 g |
| Sesame oil | 20 g |
| Isopropyl alcohol | 2 g |
| Eusolex ® | 1.5 g |
| Perfume | 0.4 g |
| SR 45583 A | 0.100 g |
| (Eusolex ® is marketed by Merck) | |

EXAMPLE 32

Preservative in a shampoo

| Potassium amino acid palmitate | 20 g |
|---|---|

| -continued | |
|---|---|
| Sodium alkylsulfates | 2 g |
| Copra diethanolamide | 5 g |
| Linalyl acetate | 0.200 g |
| SR 45583 A | 0.05 g |
| Sodium hydroxide q.s. pH 7 | |
| Purified water q.s. | 100 g |

EXAMPLE 33

Preservative for fruit juice or jam

| Micronized SR 45583 A | 0.02% |
|---|---|

EXAMPLE 34

Disinfectant for inert surfaces

| SR 45583 A | 2 g |
|---|---|
| Dodecyldimethylcarboxydimethylamine | 20 g |
| Disodium tetracemate | 2 g |
| Lactic acid q.s. pH 3.5 | |
| Purified water q.s. | 100 g |

What is claimed is:

1. An aminoalkylauramide of the formula

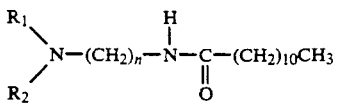

in which $R_1$ is a benzyl group and $R_2$ is an alkyl having from 1 to 4 carbon atoms, or $R_1$ and $R_2$ form a 4-benzylpiperidino group with the nitrogen atom to which they are bonded, and $n=2$ to 6, or one of its salts with organic or mineral acids.

2. An aminoalkyllauramide according to claim 1 in which $n=2$.

3. An aminoalkyllauramide according to claim 1 in which $n=3$.

4. Aminoalkyllauramide according to claim 1 which is the N-(3-benzylmethylaminopropyl) lauramide.

5. A pharmaceutical composition which contains, as the active principle, a compound according to claim 1 or one of its pharmaceutically acceptable salts, in association with a pharmaceutically acceptable excipient.

6. A pharmaceutical composition having an antimicrobial and disinfectant activity, which contains from 0.01 to 5% of the compound according to claim 1.

7. A disinfectant composition for inert surfaces, which contains from 0.1 to 4% of the compound according claim 1.

8. A pharmaceutical composition which contains, as a preservative, from 0.005 to 0.5% of the compound according claim 1.

9. A cosmetic product which contains, as a preservative, from 0.005 to 0.5% of the compound according to claim 1.

10. An edible product which contains, as a preservative, from 0.005 to 0.5% of the compound according to claim 1.

* * * * *